(12) United States Patent
Burke et al.

(10) Patent No.: US 7,797,982 B2
(45) Date of Patent: Sep. 21, 2010

(54) PERSONAL BREATHALYZER HAVING DIGITAL CIRCUITRY

(75) Inventors: Paul C. Burke, Lake Forest, IL (US); Chi Wing Wong, Hong Kong (CN)

(73) Assignees: Resource Management International, LLC, Waukegan, IL (US); Honor Tone Limited, Shatin, New Terrotories (HK)

( * ) Notice: Subject to any disclaimer, the term of this patent is extended or adjusted under 35 U.S.C. 154(b) by 46 days.

(21) Appl. No.: 11/745,854

(22) Filed: May 8, 2007

(65) Prior Publication Data
US 2008/0078232 A1 Apr. 3, 2008

Related U.S. Application Data

(60) Provisional application No. 60/746,716, filed on May 8, 2006.

(51) Int. Cl.
*G01N 33/497* (2006.01)
(52) U.S. Cl. .......................... 73/23.3; 600/532; 600/543
(58) Field of Classification Search .................. 73/23.3; 600/532, 543
See application file for complete search history.

(56) References Cited

U.S. PATENT DOCUMENTS

| | | | |
|---|---|---|---|
| 3,940,251 A | 2/1976 | Jones et al. | |
| 4,093,945 A | 6/1978 | Collier et al. | |
| 4,132,109 A | 1/1979 | VanderSyde | |
| 4,163,383 A | 8/1979 | VanderSyde et al. | |
| 4,278,636 A | 7/1981 | Voigt et al. | |
| 4,363,635 A | 12/1982 | Hutson | |
| 4,407,152 A | 10/1983 | Guth | |
| 4,770,026 A | 9/1988 | Wolf | |
| 4,905,498 A | 3/1990 | O'Donnell et al. | |
| 4,912,458 A | 3/1990 | Comeau et al. | |
| 4,914,038 A | 4/1990 | Jewitt | |
| 5,393,495 A | 2/1995 | Forrester | |
| 5,400,637 A | 3/1995 | Forrester | |
| 5,422,485 A | 6/1995 | Bowlds | |
| 6,096,558 A | 8/2000 | Stock | |
| 6,167,746 B1 | 1/2001 | Gammenthaler | |
| 6,526,802 B1 | 3/2003 | Fisher et al. | |
| 6,792,793 B2 | 9/2004 | Mendoza | |
| 6,923,040 B2 | 8/2005 | Stock | |
| 2003/0052692 A1 | 3/2003 | Lin | |
| 2003/0176803 A1 | 9/2003 | Gollar | |

OTHER PUBLICATIONS

FIS Gas Sensor SB-30 for Alcohol Detection Specifications, May 1999, 2 pages, FiS Inc., Itami, Hyogo Japan.
Figaro, Product Information, TGS 2620- for the detection of Solvent Vapors, Jan. 2005, 2 pages, Figaro Engineering Inc., Mino, Osaka Japan.
International Search Report and Written Opinion for PCT/US07/68459 mailed on Oct. 10, 2007. This PCT application has common ownership and inventors with the present U.S. Appl. No. 11/745,854.
International Search Report and Written Opinion of the International Searching Authority for PCT/US07/68454 mailed on Oct. 10, 2007. This PCT application has common ownership and inventors with the present U.S. Appl. No. 11/745,854.
Co-pending U.S. Appl. No. 11/382,197, having the same owners and inventors as this U.S. Appl. No. 11/745,854.

*Primary Examiner*—Daniel S Larkin
(74) *Attorney, Agent, or Firm*—Niro, Haller & Niro

(57) ABSTRACT

The present invention relates to a portable, personal breath tester device for testing the blood alcohol content of the user of the device. The breath tester comprises a circuit board, wherein a sensor, a liquid crystal display, and a processing unit are installed on and electrically connected to the circuit board. The processing unit receives a voltage signal from the sensor representing the blood alcohol content of the user and converts the voltage signal to a precise value that is displayed on the liquid crystal display.

4 Claims, 15 Drawing Sheets

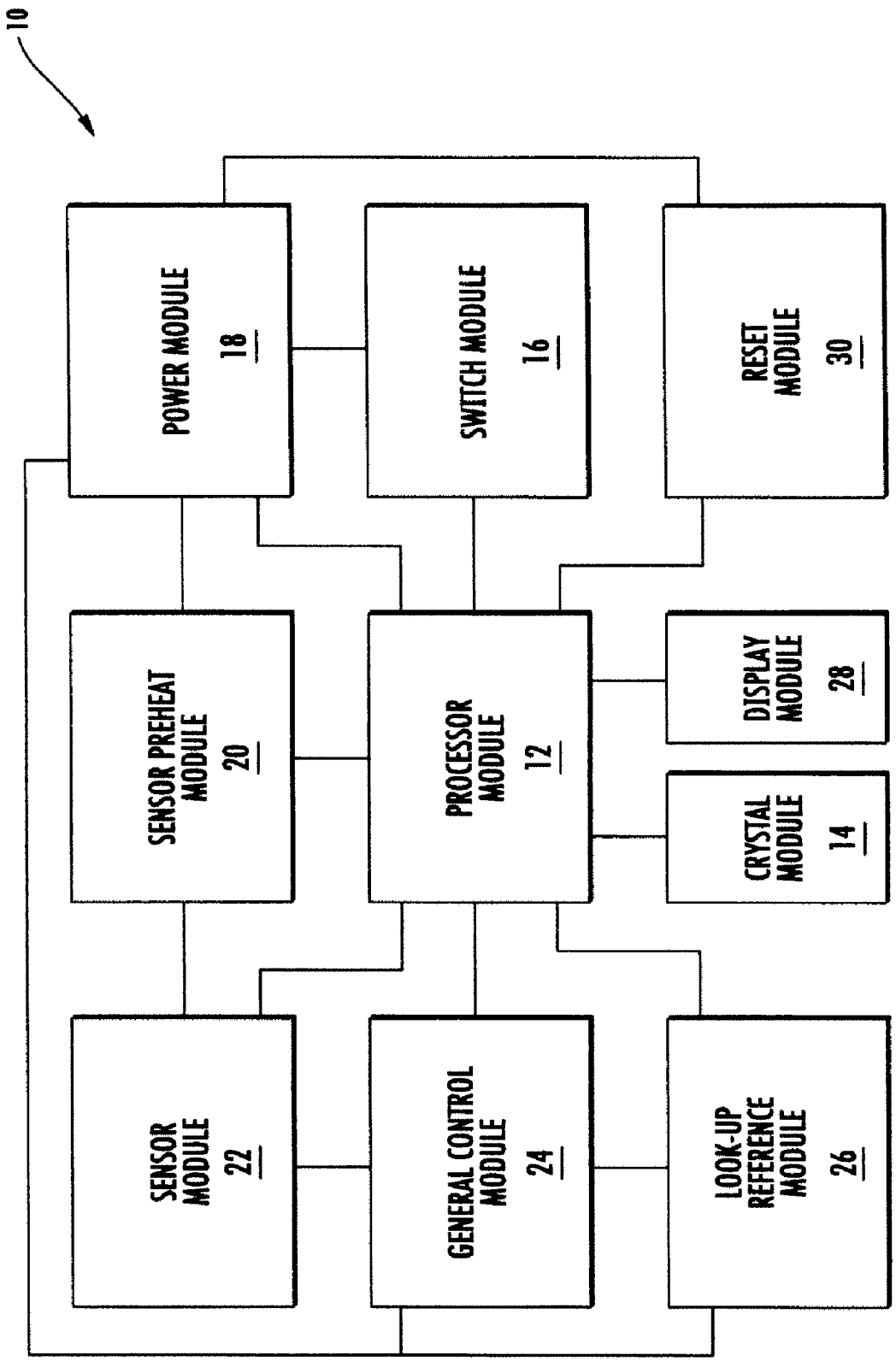

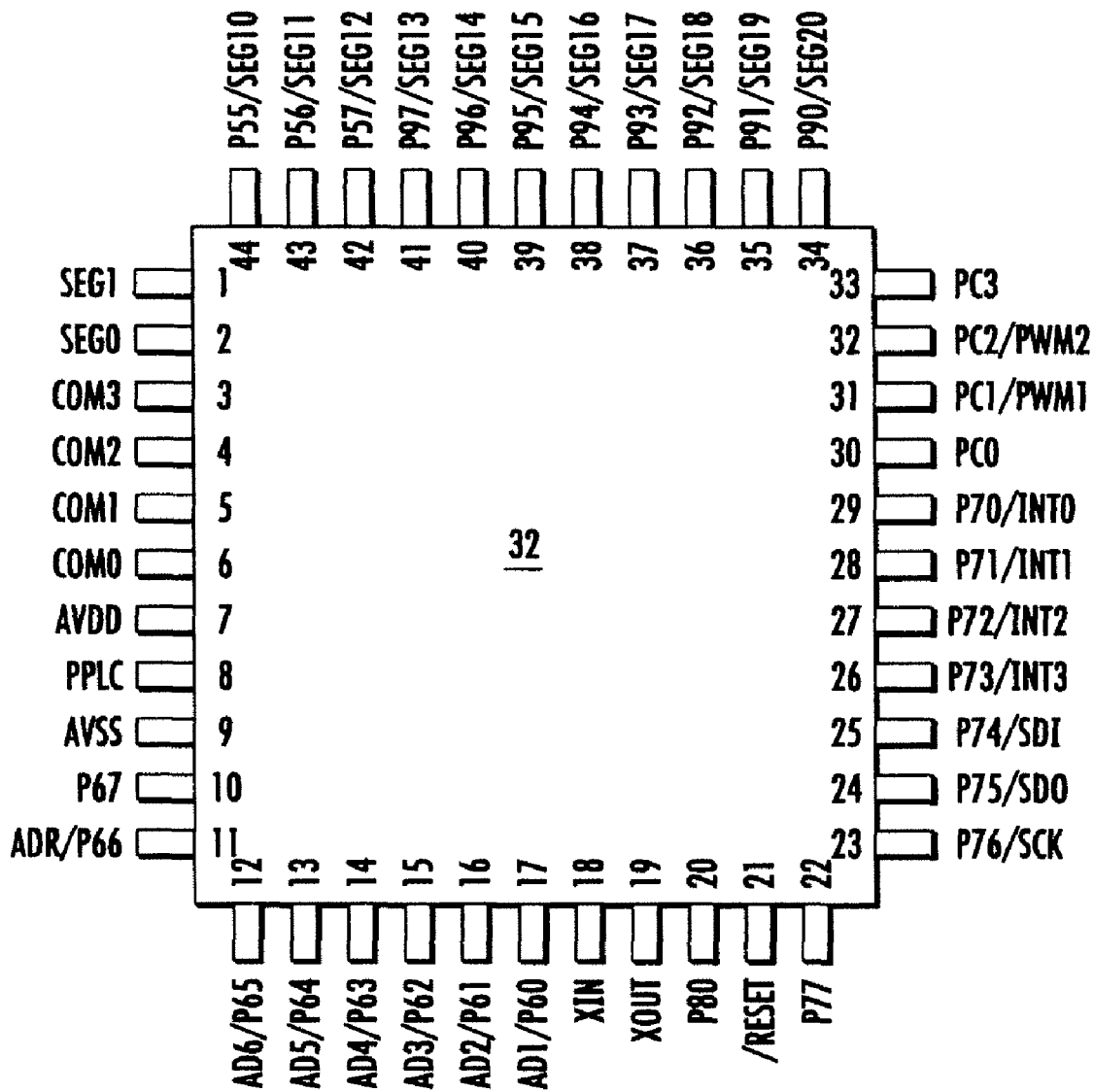
F I G . 3

| PIN | I/O | DESCRIPTION |
| --- | --- | --- |
| POWER | | |
| AVDD | POWER | POWER |
| AVSS | POWER | GROUND |
| CLOCK | | |
| XIN | I | INPUT PIN FOR 32.768 kHz OSCILLATOR |
| XOUT | O | OUTPUT PIN FOR 32.768 kHz OSCILLATOR |
| PLLC | I | PHASE LOOP LOCK CAPACITOR, CONNECT A CAPACITOR 0.01u TO 0.047u TO THE GROUND. |
| LCD | | |
| COM0 ~ COM3 | O | COMMON DRIVER PINS OF LCD DRIVERS |
| SEG0 ~ SEG1<br>SEG10 ~ SEG12<br>SEG13 ~ SEG20 | O<br>O (I/O: PORT5)<br>O (I/O: PORT9) | SEGMENT DRIVER PINS OF LCD DRIVERS<br>SEG10 TO SEG20 ARE SHARED WITH IO PORT. |
| 6 CHANNEL 10-BIT A/D | | |
| AD1 | I(P60) | ADC INPUT CHANNEL 1, SHARED WITH PORT60 |
| AD2 | I(P61) | ADC INPUT CHANNEL 2, SHARED WITH PORT61 |
| AD3 | I(P62) | ADC INPUT CHANNEL 3, SHARED WITH PORT62 |
| AD4 | I(P63) | ADC INPUT CHANNEL 4, SHARED WITH PORT63 |
| AD5 | I(P64) | ADC INPUT CHANNEL 1, SHARED WITH PORT64 |
| AD6 | I(P65) | ADC INPUT CHANNEL 2, SHARED WITH PORT65 |
| ADR | I(P66) | ADC EXTERNAL REFERENCE INPUT, SHARED WITH PORT66 |
| SPI | | |
| SCK | IO (PORT76) | MASTER: OUTPUT PIN, SLAVE: INPUT PIN. THIS PIN SHARED WITH PORT76. |
| SDO | O (PORT75) | OUTPUT PIN FOR SERIAL DATA TRANSFERRING. THIS PIN SHARED WITH PORT75. |
| SDI | I (PORT74) | INPUT PIN FOR RECEIVING DATA. THIS PIN SHARED WITH PORT74. |
| PWM | | |
| PWM1 | O (PC1) | PULSE WIDTH MODULATION OUTPUT CHANNEL 1. THIS PIN SHARED WITH PC1 |
| PWM2 | O (PC2) | PULSE WIDTH MODULATION OUTPUT CHANNEL 2. THIS PIN SHARED WITH PC2 |
| IO | | |
| P55~P57 | I/O | PORT5 CAN BE INPUT OR OUTPUT PORT EACH BIT.<br>PORT5(7:5) ARE SHARED WITH LCD SEGMENT SIGNAL. |
| P60~P67 | I/O | PORT6 CAN BE INPUT OR OUTPUT PORT EACH BIT. |
| P70~P77 | I/O | PORT7 CAN BE INPUT OR OUTPUT PORT EACH BIT.<br>PORT7(4~6) ARE SHARED WITH SPI INTERFACE PINS<br>INTERNAL PULL HIGH FUNCTION.<br>PORT7(0~3) HAS INTERRUPT FUNCTION. |
| P80 | I/O | P80 CAN BE INPUT OR OUTPUT PORT EACH BIT.<br>INTERNAL PULL HIGH.<br>PORT80 HAVE WAKE-UP FUNCTIONS(SET BY RE PAGE0) |
| P90~P97 | I/O | PORT9 CAN BE INPUT OR OUTPUT PORT EACH BIT.<br>PORT90~93 ARE SHARED WITH ADC INPUT.<br>PORT9 ARE SHARED WITH LCD SEGMENT SIGNAL |
| PC0~PC3 | I/O | PORTC CAN BE INPUT OR OUTPUT PORT EACH BIT.<br>PORTC(1~2) ARE SHARED WITH PWM OUTPUT PINS |
| INT0 | (PORT70) | INTERRUPT SOURCES. ONCE PORT70 HAS A FALLING EDGE OR RISING EDGE SIGNAL (CONTROLLED BY CONT REGISTER), IT WILL GENERATE A INTERRUPTION. |
| INT1 | (PORT71) | INTERRUPT SOURCES WHICH HAS THE SAME INTERRUPT FLAG. ANY PIN FROM PORT71 HAS A FALLING EDGE SIGNAL, IT WILL GENERATE A INTERRUPTION. |
| INT2 | (PORT72) | INTERRUPT SOURCES WHICH HAS THE SAME INTERRUPT FLAG. ANY PIN FROM PORT72 HAS A FALLING EDGE SIGNAL, IT WILL GENERATE A INTERRUPTION. |
| INT3 | (PORT73) | INTERRUPT SOURCES WHICH HAS THE SAME INTERRUPT FLAG. ANY PIN FROM PORT73 HAS A FALLING EDGE SIGNAL, IT WILL GENERATE A INTERRUPTION. |
| /RESET | I | LOW RESET |

FIG. 4

PC1/PWM1 OUT WAVEFORM

COLLECTOR OF Q3 OUTPUT WAVEFORM

COLLECTOR OF Q2 OUTPUT WAVEFORM

| PIN NAMES | PIN TYPE | PIN DESCRIPTION | CIRCUIT NUMBER | PIN NUMBERS | SHARE PINS |
|---|---|---|---|---|---|
| P0.0<br>P0.1<br>P0.2<br>P0.3 | I/O | 1-BIT PROGRAMMABLE I/O PORT. SCHMITT TRIGGER INPUT OR PUSH-PULL, OPEN-DRAIN OUTPUT AND SOFTWARE ASSIGNABLE PULL-UPS. | E-4 | 39(3)<br>40(4)<br>41(5)<br>42(6) | TAOUT/INT<br>T1CLK/INT<br>INT<br>BUZ/INT |
| P0.4-P0.5 | O | 1-BIT PROGRAMMABLE OUTPUT PORT. | C | 43-44 | |
| P1.0<br>P1.1<br>P1.2<br>P1.3 | I/O | 1-BIT PROGRAMMABLE I/O PORT. SCHMITT TRIGGER INPUT OR PUSH-PULL, OPEN-DRAIN OUTPUT AND SOFTWARE ASSIGNABLE PULL-UPS. | F-16A | 1(7)<br>2(8)<br>3(9)<br>4(10) | AD0/INT<br>AD1/INT<br>AD2/INT<br>AD3/INT |
| P2.0<br>P2.1 | I/O | 1-BIT PROGRAMMABLE I/O PORT. SCHMITT TRIGGER INPUT OR PUSH-PULL, OPEN-DRAIN | H-32A | 16(22)<br>15(21) | SCK/SEG1<br>SO/SEG0 |
| P2.2<br>P2.3 | I/O | OUTPUT AND SOFTWARE ASSIGNABLE PULL-UPS. | E-4 | 14(20)<br>13(19) | SI<br>— |
| P3.0<br>P3.1 | I/O | 1-BIT PROGRAMMABLE I/O PORT. SCHMITT TRIGGER INPUT OR PUSH-PULL, OPEN-DRAIN OUTPUT AND SOFTWARE ASSIGNABLE PULL-UPS. | H-32B | 18(24)<br>17(23) | INTP/SEG3<br>INTP/SEG2 |
| P4.0-P4.7 | I/O | 1-BIT PROGRAMMABLE I/O PORT. INPUT OR PUSH-PULL, OPEN-DRAIN OUTPUT AND SOFTWARE ASSIGNABLE PULL-UPS | H-32 | 19-26(25-32) | SEG4-SEG11 |
| P5.0-P5.3 | I/O | 1-BIT PROGRAMMABLE I/O PORT. INPUT OR PUSH-PULL, OPEN-DRAIN OUTPUT AND SOFTWARE ASSIGNABLE PULL-UPS | H-32 | 27-30(33-36) | SEG12-SEG15 |
| P5.4-P5.7 | | | | 31-34(37-40) | SEG16-SEG19/COM7-COM4 |
| P6.0-PP6.3 | I/O | 1-BIT PROGRAMMABLE I/O PORT. INPUT OR PUSH-PULL, OPEN-DRAIN OUTPUT AND SOFTWARE ASSIGNABLE PULL-UPS | H-32 | 35-38<br>(41-42,1-2) | COM3-COM0 |

FIG. 10a

| PIN NAMES | PIN TYPE | PIN DESCRIPTION | CIRCUIT NUMBER | PIN NUMBERS | SHARE PINS |
|---|---|---|---|---|---|
| $V_{DD}, V_{SS}$ | — | POWER INPUT PINS FOR INTERNAL POWER BLOCK | — | 5,6(11,12) | — |
| $X_{OUT}, X_{IN}$ | — | MAIN OSCILLATOR PINS FOR MAIN CLOCK | — | 7,8(13,14) | — |
| $XT_{OUT}, XT_{IN}$ | — | SUB OSCILLATOR PINS FOR SUB CLOCK | — | 11,10(17,16) | — |
| TEST | — | CHIP TEST INPUT PIN HOLD GND WHEN THE DEVICE IS OPERATIING | — | 9(15) | — |
| RESET | I | RESET SIGNAL INPUT PIN. SCHMITT TRIGGER INPUT WITH INTERNAL PULL-UP RESISTOR. | B | 12(18) | — |
| INT | I/O | EXTERNAL INTERRUPTS INPUT. | E-4 F-16A | 39-42(3-6) 1-4(7-10) | P0.0-P0.3 P1.0-P1.3 |
| INTP | I/O | KEY SCAN INTERRUPTS INPUTS. | H-32B | 17-18(23-24) | P3.1-P3.0 |
| TICLK | I/O | TIMER 1/A EXTERNAL CLOCK INPUT. | E-4 | 40(4) | P0.1 |
| TAOUT | I/O | TIMER 1/A CLOCK OUTPUT. | E-4 | 39(3) | P0.0 |
| AD0-AD3 | I/O | ANALOG INPUT PINS FOR A/D CONVERTS MODULE. | F-16A | 1-4(7-10) | P1.0-P1.3 |
| BUZ | I/O | BUZZER SIGNAL OUTPUT. | E-4 | 42(6) | P0.3 |
| SCK SO | I/O | SERIAL CLOCK, SERIAL DATA OUTPUT, SERIAL DATA INPUT | H-32A | 16-15(22-21) | P2.0-P2.1 |
| SI | | | E-4 | 40(20) | P2.2 |
| SEG0-SEG1 | I/O | LCD SEGMENT SIGNAL OUTPUT | H-32A | 15-16(21-22) | P2.1-P2.0 |
| SEG2-SEG3 | | | H-32B | 17-18(23-24) | P3.1-P3.0 |
| SEG4-SEG19 | | | H-32 | 19-34(25-40) | P4.0-P4.7 P5.0-P5.7 |
| COM0-COM7 | I/O | LCD COMMON SIGNAL OUTPUT | H-32 | 38-31 (2-1,42-37) | P6.3-P6.0 P5.7-P5.4 |

Fig. 10 b

PERSONAL BREATHALYZER HAVING DIGITAL CIRCUITRY

CROSS-REFERENCE TO RELATED APPLICATIONS

This application claims the benefit of U.S. provisional patent application No. 60/746,716, filed on May 8, 2006.

BACKGROUND OF THE INVENTION

1. Field of the Invention

The present invention relates the gaseous breath detection devices, and methods for using the same, and more particularly to a portable personal gaseous breath detection device incorporating digital circuitry to analyze a sample of alveolar air from the user of the device for the presence of alcohol.

2. Background Art

The present invention relates generally to devices and methods for determining the concentration of alcohol in a mixture of gases and more particularly, the invention relates to a device and method for determining the concentration of alcohol in a breath sample for application in sobriety detection systems.

Various techniques have been employed for calculating a person's blood alcohol concentration by measuring breath samples. A first method employs an infrared absorption technique for determining the blood alcohol concentration. Breath alcohol levels are measured by passing a narrow band of IR light, selected for its absorption by alcohol, through one side of a breath sample chamber and detecting emergent light on the other side. The alcohol concentration is then determined by using the well-known Lambert-Beers law, which defines the relationship between concentration and IR absorption. This IR technology has the advantage of making real-time measurements; however, it is particularly difficult and expensive to achieve specificity and accuracy at low breath alcohol concentration levels. Also, the IR detector output is nonlinear with respect to alcohol concentration and must be corrected by measurement circuits.

A second method employs a fuel cell together with an electronic circuit. In breath alcohol testing devices presently used commercially, in which fuel cells are employed, the conventional way of determining breath alcohol is to measure a peak voltage across a resistor due to the flow of electrons obtained from the oxidation of breath alcohol on the surface of the fuel cell. Although this method has proven to have high accuracy levels, there are a number of problems. The peaks become lower with repeated use of the fuel cell and vary with different temperatures. In order to produce a high peak, it is customary to put across the output terminals of the fuel cell a high external resistance, on the order of a thousand ohms, but the use of such a high resistance produces a voltage curve which goes to the peak and remains on a high plateau for an unacceptably long time. To overcome that problem, fuel cell systems began to short the terminals, which drops the voltage to zero while the short is across the terminals. However, it is still necessary to let the cell recover, because if the short is removed in less than one-half to two minutes after the initial peak time, for example, the voltage creeps up. Peak values for the same concentration of alcohol decline with repeated use whether the terminals are shorted or not, and require 15-25 hours to recover to their original values.

In addition, individual fuel cells differ in their characteristics. All of them slump with repeated use in quick succession and also after a few hours' time of non-use. They degrade over time, and in the systems used heretofore, must be re-calibrated frequently. Eventually, they degrade to the place at which they must be replaced. Presently, the cell is replaced when it peaks too slowly or when the output at the peak declines beyond practical re-calibration, or when the background voltage begins creeping excessively after the short is removed from the cell terminals.

Systems employing this method were also cost prohibitive for many applications. One reason for the high cost associated with the fuel cell techniques is that the method requires that the breath sample be of a determinable volume. Historically, this has been accomplished through the use of positive displacement components such as piston-cylinder or diaphragm mechanisms. The incorporation of such components within an electronic device necessarily increases the costs associated with the device.

In a third method, the alcohol content in a breath sample is measured using a semiconductor sensor commonly referred to as a Tagucci cell. Among the advantages of devices utilizing semiconductor sensors are simplicity of use, light weight, and ease of portability and storage. Such units have been employed in law enforcement work as "screening units," to provide preliminary indications of a blood alcohol content and for personal use. Although this method provides a low cost device, instruments incorporating this method have proved to have poor accuracy because of the need to hold input voltage signals to the electronic components of the device at constant, steady, regulated levels.

Accordingly, it is desirable to have a breath test device that is easy to use yet accurate in its results, is portable and is an item that the user will remember to bring with him/her to an event or location where alcohol is being consumed.

BRIEF SUMMARY OF THE INVENTION

The present invention provides a electronic breath analyzer. The electronic breath analyzer includes a gas sensor for alcohol detection. The gas sensor having a heater and a gas sensing element. A micro controller including a general control output, a reference value input and a gas sensing element input. The gas sensing element input is coupled to the gas sensing element. The micro controller is adapted to provide an initiate reading and comparison signal at the general control output. A reference value register includes a reference value in the register, and having a read initiate input and a reference value output. A general control module includes a control input, a read register output, and an enable gas sensor output. The control input is coupled to the general control output, the read register output is coupled to the read initiate input and provides a read initiate signal upon receiving the initiate reading and comparison signal at the general control module. The enable gas sensor output is coupled to the gas sensor and produces an enable signal upon receiving the initiate reading and comparison signal at the general control module.

In one embodiment, the general control module includes an NPN transistor having an emitter coupled to VCC, the base coupled to the micro controller, and the collector is coupled to the sensing element through a resistor, and the collector is also coupled to VCC of a memory chip to enable shifting serial reference data to the micro controller. Concurrently, the micro controller produces a clock signal at the clock input of the memory chip.

In one embodiment, a first and second stage transistor circuit is provided to amplify current coupled to the gas sensor.

BRIEF DESCRIPTION OF THE SEVERAL VIEWS OF THE DRAWINGS

FIG. 1 shows a block diagram of a breath tester system according to a preferred embodiment of the present invention;

FIG. 3 shows detailed schematic of the pin configuration of the microprocessor of a preferred embodiment of the present invention;

FIG. 4 is a table providing details of the pins of the microprocessor of FIG. 3;

FIGS. 10a-10b are tables providing details of the pins of the microprocessor of FIG. 9.

DETAILED DESCRIPTION OF THE INVENTION

Figure 2A:
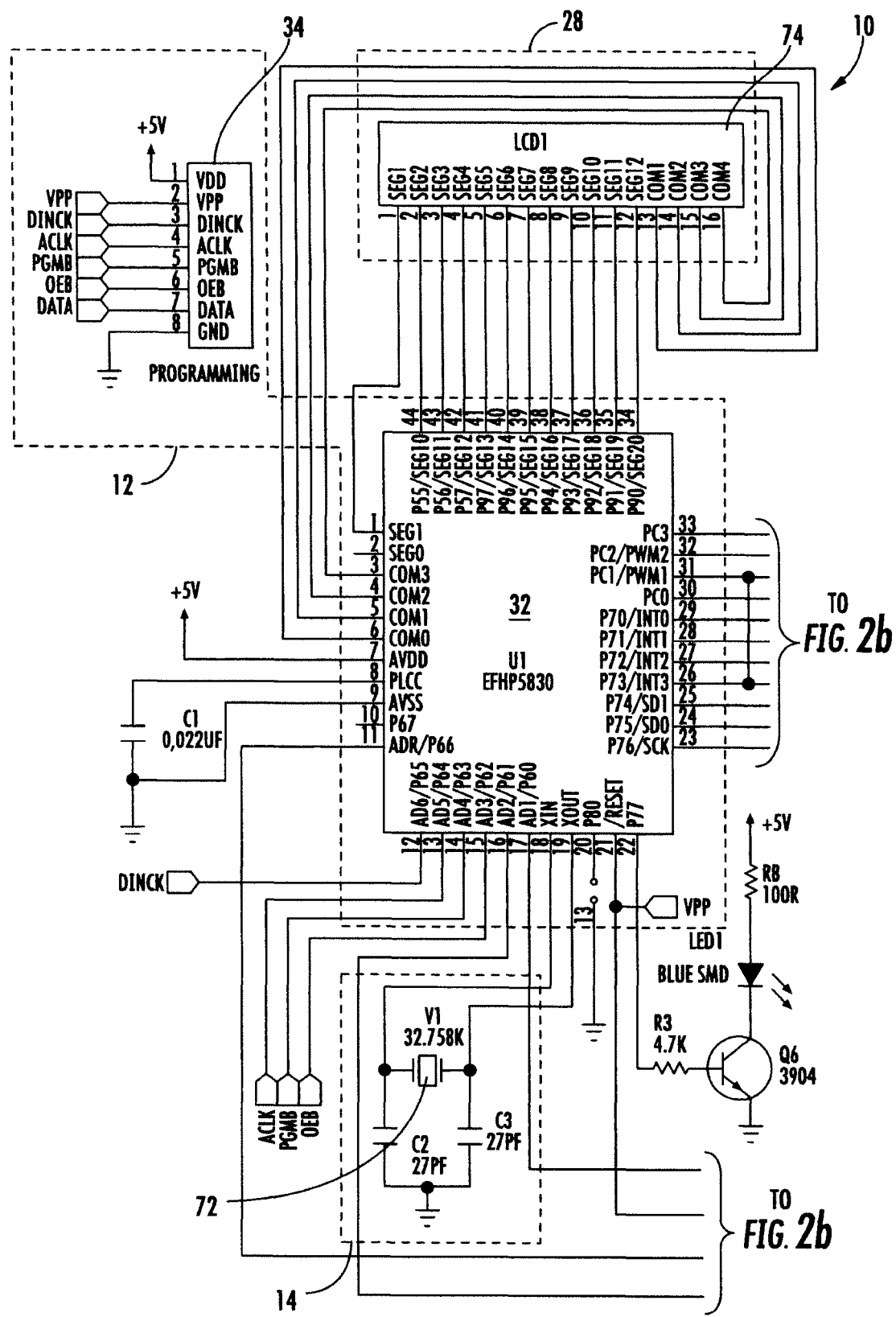
FIGS. 2a-c show a circuit schematic diagram of a breath tester system according to a preferred embodiment of the present invention.

FIGS. 1 and 2 show a breath tester device 10 in accordance with a first preferred embodiment of the present invention for testing a breath sample from the user of the device and calculating the blood alcohol content of the breath sample. As is seen in the block diagram of FIG. 1 and the circuit schematic of FIG. 2, the breath tester 10 comprises the following modules: Processor Module 12; Crystal Module 14; Switch Module 16; Power Module 18; Sensor Preheat Module 20; Sensor Module 22; General Control Module 24; Look-Up Reference Module 26; Display Module 28; and Reset Module 30. The individual modules have been organized and named for purposes of convenience in describing the structure and arrangement of components in this preferred embodiment and should not be considered as limiting in any manner.

As is seen in FIG. 1, the Processor Module 12 is central to and electrically coupled to the remaining modules. In addition, the Power Module 18 is also coupled to the Sensor Preheat Module 20. The Sensor Preheat Module 20 is in turn coupled to the Sensor Module 22. The Sensor Module 22 is coupled to the General Control Module 24, which is coupled to the Look-Up Reference Module 26.

The circuit elements of the modules shown in FIG. 1 will now be described in greater detail. The Processor Module 12 is composed of a microprocessor chip 32 and programming unit 34. In a preferred embodiment of the present invention, the microprocessor 32 comprises an 8-bit RISC type chip with low power, high speed CMOS technology and having 16K×13 bits of internal memory. The microprocessor 32 further comprises an on-chip watchdog timer, program ROM, data RAM, LCD driver, programmable real time clock/counter, internal interrupt, power down mode, built-in three-wire SPI, dual PWM (Pulse Width Modulation), 6-channel 10 bit A/D converter, and tri-state I/O. FIG. 3 shows the pin configuration of microprocessor 32 in detail and FIG. 4 shows a table providing additional description of each pin on the microprocessor 32. The microprocessor 32 used in a preferred embodiment of the present invention is manufactured by Elan Microelectronics Corp. and is sold as Product No. eFH5830AD. However, any suitable microprocessor can be utilized for purposes of the present invention.

Figure 2B:
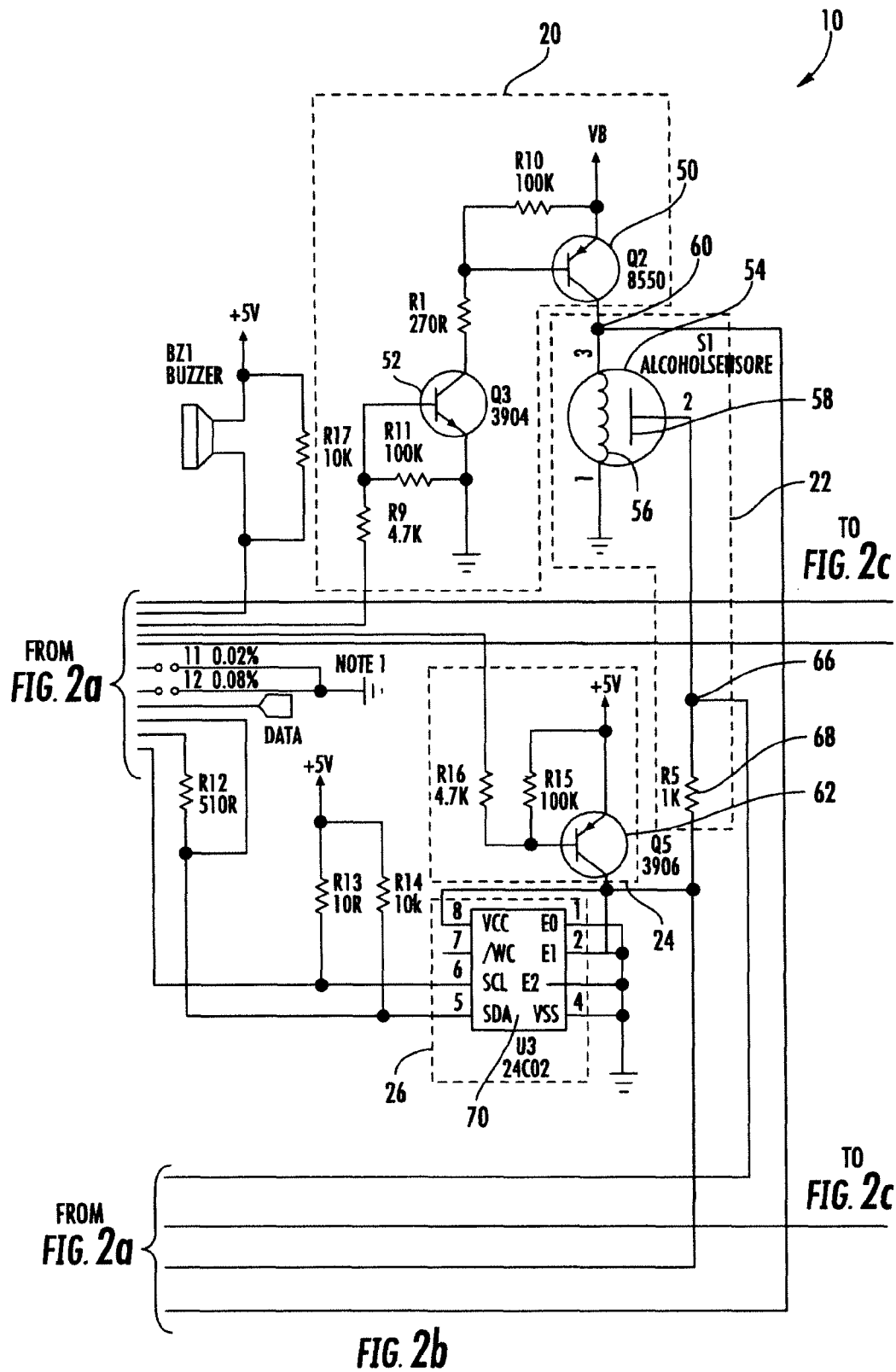
Figure 2C:
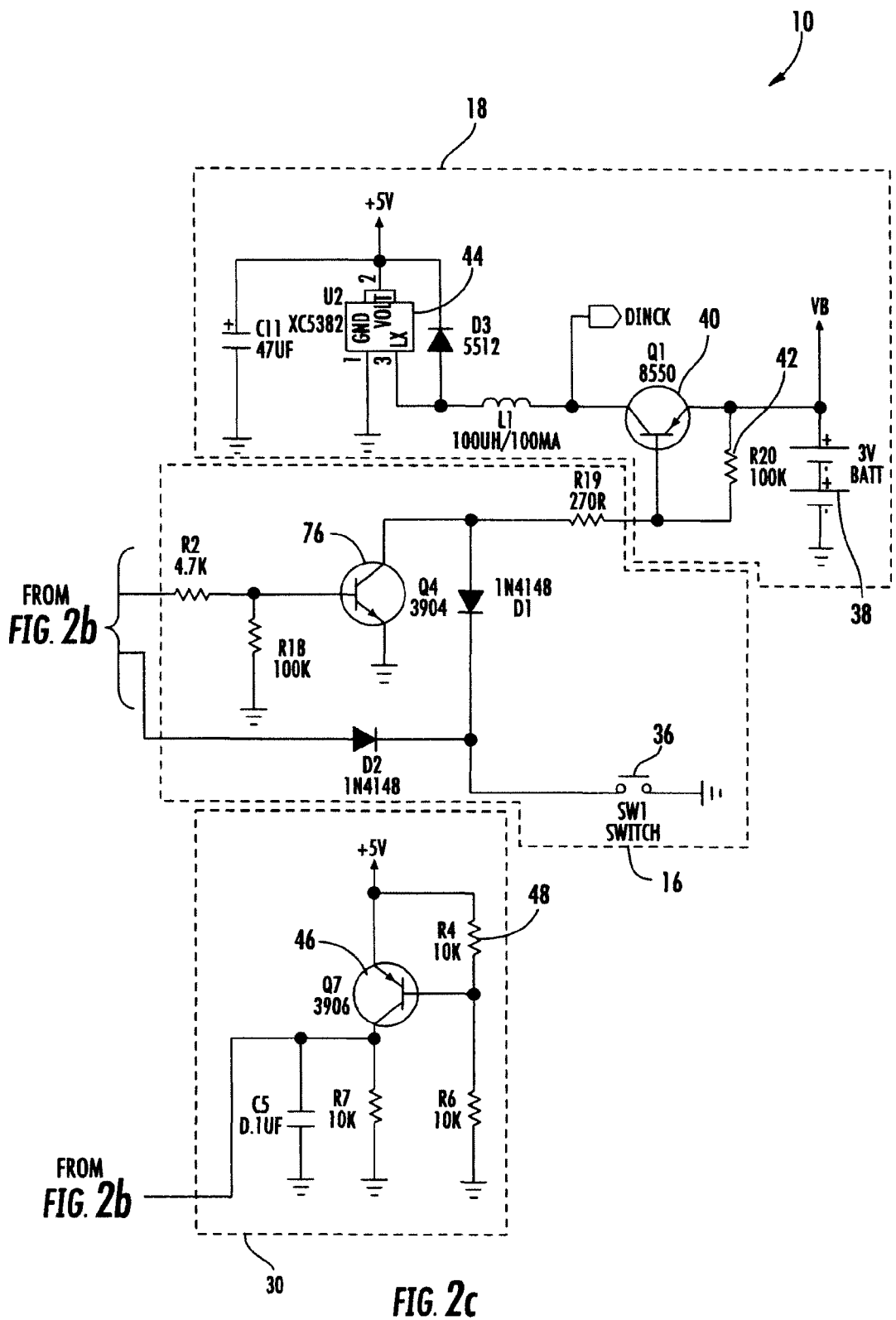

Referring to the operation of the Switch Module 16 and Power Module 18 (as shown in FIG. 2c), depressing the switch 36 will ground the positive terminal of the power source 38 causing a voltage to flow along the established pathway. The emitter end of the transistor 40 is coupled directly to the positive terminal of power source 38 and therefore receives voltage Vb from the power source 38. The base of the transistor 40 is also coupled to the positive terminal of power source 38 across resistor 42. Accordingly the base end of transistor 40 receives a voltage of Vb minus the voltage drop across resistor 42. Because transistor 40 is in a P-N-P configuration and the voltage at the base is less than the voltage at the emitter, the transistor is biased closed, coupling the emitter and collector of transistor 40 and enabling Vb minus the voltage drop across transistor 40 to flow towards the step-up converter 44.

The step-up converter 44, steps up the input voltage signal to a voltage of +5V. In another preferred embodiment of the present invention, shown in FIG. 8b and described in detail below, the step-up converter 44 steps up the input voltage signal to a voltage of +4V. The +5V voltage signal generated by the Power Module 18 is coupled to the components of the Processor Module 12 via the AVDD power pin (Port 7), the General Control Module 24, the Look-Up Reference Module 26, and the Reset Module 30. Voltage Vb from the power source 38 is coupled to the Sensor Preheat Module 20. In a preferred embodiment of the present invention the step-up converter 44 is a PFM controlled, step-up DCIDC converter manufactured by Torex Semiconductor and is sold under Product Number XC6382. The power source in this embodiment of the present invention is a 3V DC battery.

The Switch Module 16 (shown in FIG. 2c) also comprises an "electronic" switch that, when triggered, will enable the power source 38 to provide voltage to the device 10 if the user of the device releases the switch 36. The base of transistor 76 is coupled to the PC3 input/output pin (Port 33) of microprocessor 32. Once powered up, the microprocessor 32 generates and sends an output voltage signal to the base of the transistor 76. Because transistor 76 is configured in the N-P-N configuration and the emitter is coupled to ground, the output voltage signal causes the transistor 76 to be biased closed, coupling the emitter and collector. Because the collector of transistor 76 is coupled to the base of the transistor 40, transistor 76 serves as an electronic switch, keeping transistor 40 biased closed to enable Vb from the positive terminal of power source 38 to supply a voltage to the Sensor Preheat Module 20 and the step-up converter 44. When the switch 36 is released and the microprocessor 32 terminates the power signal sent to the base of the base of transistor 76, then the power source 38 will no longer provide voltage to the components of the device 10. The microprocessor 32 includes an automatic shut-off routine that terminates the power signal sent to the base of the transistor 76 after a preset term of inactivity.

Turning to the Reset Module 30 (shown in FIG. 2c), the emitter of transistor 46 is coupled directly to the +5V voltage signal from the step-up converter 44 of the Power Module 18. The voltage at the base of the transistor 46 comprises the +5V voltage signal from the step-up converter 44 minus the voltage drop across resistor 48. Because transistor 46 is in a P-N-P configuration, the transistor 46 is biased closed, coupling the emitter and collector and sending an input signal to the RESET pin (Port 21) of microprocessor 32 causing the breath tester circuit to reset itself and prepare to take a new reading.

Figure 5A:
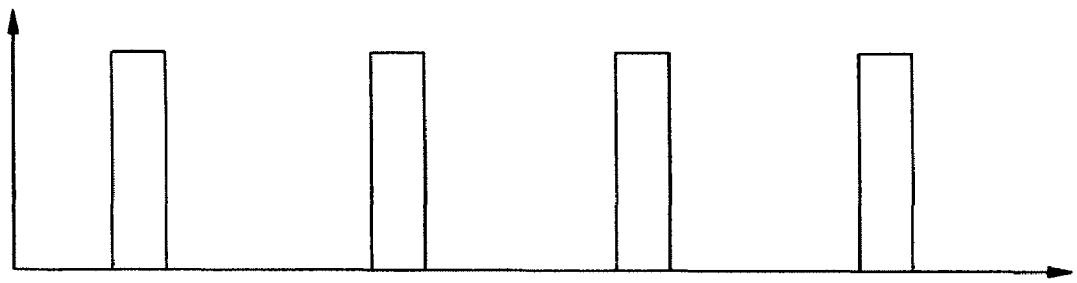
FIGS. 5a-c show graphical representations of output waveforms of voltage (vertical axis) over time (horizontal axis) of electrical components of a preferred embodiment of the present invention.
Figure 5B:
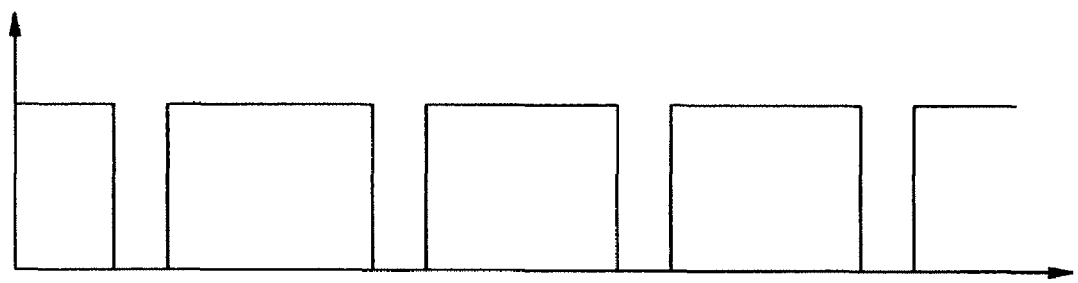
Figure 5C:
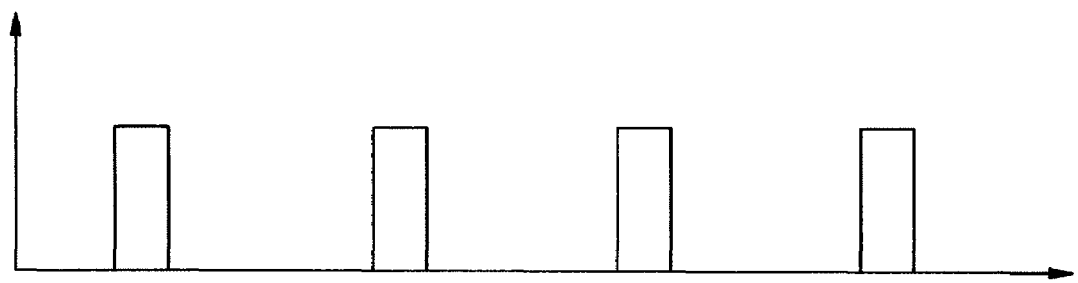

Turning to the Sensor Preheat Module 20 (shown in FIG. 2b), at one end of the module 20, the emitter of transistor 50 is coupled directly to the positive terminal of power source 38 and, therefore, has a voltage of Vb. The second end of the Sensor Preheat Module 20 is coupled to the PCIIPWMI pin (Port 31) of the microprocessor 32 and receives a power signal from the microprocessor 32. The breath tester circuit utilizes the pulse width modulation function of the microprocessor 32 to control transistors 50 and 52 of the Sensor Preheat Module 20 and provide to the Sensor Module 22 constant voltage with a high current. The transistor 52 is configured in the N-P-N configuration with the emitter coupled to ground. Accordingly, providing a positive voltage signal to the base of transistor 52 will bias the transistor 52 closed, coupling the base of transistor 52 to ground. The base of transistor 50 is also coupled to the collector of transistor 52 and is therefore responsive to the voltage signal at the collector of transistor 52. As is seen in the waveform diagrams of FIGS. 5a-5c, when the microprocessor 32 provides a pulse voltage signal to the Sensor Preheat Module 20 through the PCIIPWMI pin, the transistor 52 is biased closed and the voltage at the collector is coupled to ground. Because the transistor 50 is in a P-N-P configuration, when the voltage at the base of transistor 50 is coupled to ground via transistor 52, the transistor 50 is biased closed, coupling the emitter and collector and providing a steady voltage to the Sensor Module 22. The Pulse Width Modulation signal sent by the microprocessor 32 controls the operation of transistors 50 and 52 to provide a 0.9V equivalent DC voltage to the Sensor Module 22.

In a preferred embodiment of the present invention, the Sensor Module 22 comprises a tin dioxide semiconductor gas sensor 54. Tin dioxide sensors have high sensitivity to the presence of alcohol, however, it is contemplated that other suitable gas sensors are available and can be utilized in the present invention. The sensor 54 comprises a heating element 56 and a sensor element 58. The heating element 56 comprises a resistor having a first end coupled to the voltage output of the Sensor Preheat Module 20 and a second end coupled to ground. The sensing element 58 comprises a variable resistor having a conductivity that varies depending on the temperature of the sensor and the concentration of alcohol vapors present. A tin dioxide gas sensor manufactured by FiS, Inc. of Japan and is sold under Product Number SB-30 is utilized in this preferred embodiment of the present invention.

In order to obtain optimum performance from the sensor 54 the voltage applied across the heating element 56 must be held steady. The sensor 54 of the present invention exhibits optimum performance when a voltage of 0.9V is applied to the heating element 56. As previously described, the components of the Sensor Preheat Module 20 are selected to provide a constant 0.9V to the heating element during operation of the breath test device 10 of the present invention. Reference point 60 is coupled to microprocessor 32 at AD2/P61 input pin (Port 16) to enable the microprocessor 32 to monitor the voltage at reference point 60.

The sensing element 58 operates at a circuit voltage of preferably less than 5V. The sensor 54 output is also controlled by the transistor 62 of the General Control Module 24. The emitter of transistor 62 is coupled to the output of the step-up converter 44 of the Power Module 18 and is at a voltage of 5V. Whereas transistor 62 is configured in a P-N-P configuration, the emitter will be coupled to the collector when the 5V power signal is applied to the emitter. By controlling the voltage to the output terminal of the sensor 54, transistor 62 is controlling the output power signal of sensor 54. The output signal representing the voltage at the sensing element 58 is measured at reference point 66 adjacent to load resistor 68 and is coupled to the microprocessor 32 at the ADI/P60 input pin (Port 17) for monitoring by the microprocessor 32.

The transistor 62 also controls the voltage (Vcc) to the memory 70 of the Look-Up Reference Module 26. In a preferred embodiment, the memory 70 comprises an electrically erasable and programmable read-only memory (EEPROM) unit having at least 2048 bits of serial memory. An EEPROM suitable for use in the present invention is manufactured by Atmel Corp. and sold under Product No. AT2402C. The EEPROM 70 is used to store calibration data and look-up tables utilized by the microprocessor 32 during operation of the breath test device 10. EEPROM 70 comprises a plurality of memory locations which serve as individually addressable reference registers containing values for the microprocessor to compare against the output of the sensing element during calibration and operation of the electronic breath analyzer. The EEPROM is coupled to the base of transistor 62 and operates at a voltage (Vcc) provided by and controlled by transistor 62.

The EEPROM 70 is used to store calibration and look-up table information used by the microprocessor 32 to calculate the blood alcohol content from the output voltage signal of the sensing element 58. The breath tester device 10 is calibrated prior to use and may be recalibrated with new calibration and look-up table information being entered at the programming unit 34 and stored on the EEPROM 70. Data stored on the EEPROM 70 is clocked out to the microprocessor 32 at Serial Data (SDA) pin in response to receiving clocking input signals from the microprocessor 32 at the Serial Clock (SCL) pin. The SDA pin of the EEPROM 70 is coupled to the P76/SCK pin (Port 23) of the microprocessor 32. The SCL pin of the EEPROM 70 is coupled to the P74/SDI input pin (Port 25) and P75/SDO output pin (Port 24) of the microprocessor 32.

The speed of the microprocessor 32, and in turn the clocking signal generated by the microprocessor 32 and received by the EEPROM 70, is determined by the oscillation of the crystal 72 of the Crystal Module 14. It is contemplated that any suitable crystal can be used in the present invention. While in this embodiment of the present invention, the memory 70 is a separate component than the microprocessor 32, it is contemplated that a microprocessor with sufficient internal memory can be utilized to perform the same functions as the separate memory and microprocessor configuration described herein.

The microprocessor 32 is also coupled to a Display Module 28 (shown in FIG. 2a). In a preferred embodiment of the present invention, the Display Module 28 comprises a liquid crystal display (LCD) 74. After performing the comparison of the data collected at reference point 60 against the date stored in EEPROM 70, the microprocessor 32 will cause the appropriate output to be displayed on the LCD 74. The LCD 74 is also used to display messages to the user of the device 10, as will be described in detail below.

Figure 6:
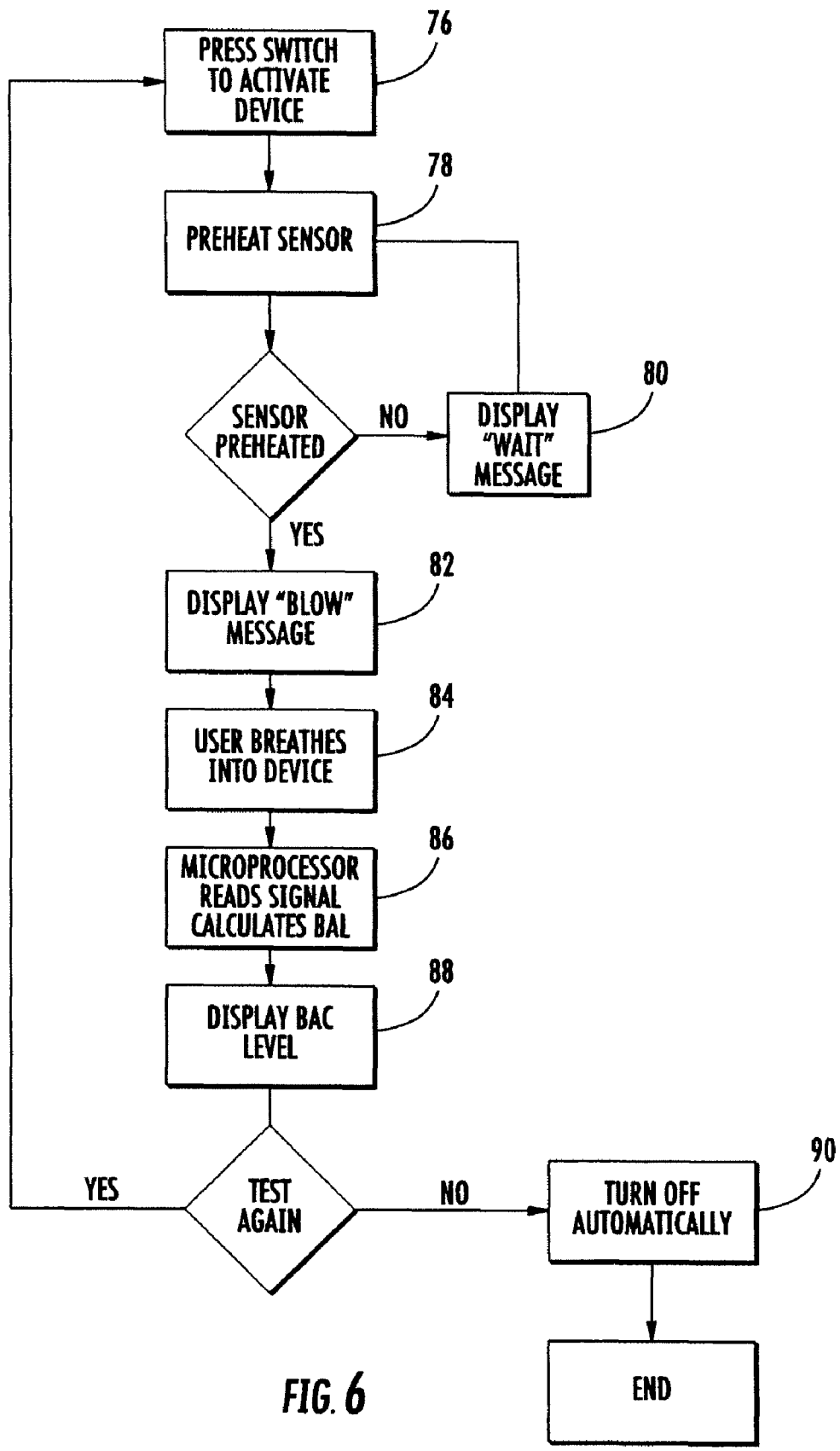
FIG. 6 shows a flow diagram of a breath tester system according to a preferred embodiment of the present invention in operation.

Referring now to FIG. 6, along with FIGS. 1 and 2, a flow chart showing operation of the breath test device 10 of the present invention is shown. The first step of operation 76 of the device 10 is to depress the switch 36 causing the Preheat Sensor Module 20 to warm up the Sensor Module 22 to proper operating temperature (78, FIG. 6). While the Sensor Module 22 is warming up 78, the microprocessor 32 sends output signals to the LCD 74 causing the LCD 74 to display a WAIT message 80 to the user of the device 10. When the Sensor Module 22 is at the proper operating temperature, the microprocessor 32 will send output signals to the LCD 74 causing the LCD 74 to display a BLOW message 82 to the user of the device 10, indicating to the user that the unit is ready to be used. Next, the user of the device 10 will blow on the Sensor Module 22 for three seconds (84, FIG. 6) to ensure that the sensing element 58 is exposed to a sufficient volume of alveolar air to take a proper reading. The Sensor Module 22 generates an output signal that is sent to the microprocessor 32 for comparison against stored values from the EEPROM 70 to determine the alcohol content of the sample of air (86, FIG. 6). Once the comparison and calculation is performed by the microprocessor 32, the microprocessor 32 generates and sends the appropriate output signals to the LCD 74, causing the LCD 74 to display the calculated blood alcohol level in units between 0.02% and 0.0%, in increments of 0.01% (88, FIG. 6).

If the user of the device 10 desires to have additional readings taken, the user will depress the switch 36 (76, FIG. 6) causing the system to reset for a subsequent reading. If the user does not test subsequent samples, the microprocessor 32 will automatically shut the device 10 off after a preset period of time (90, FIG. 6).

Figure 7:
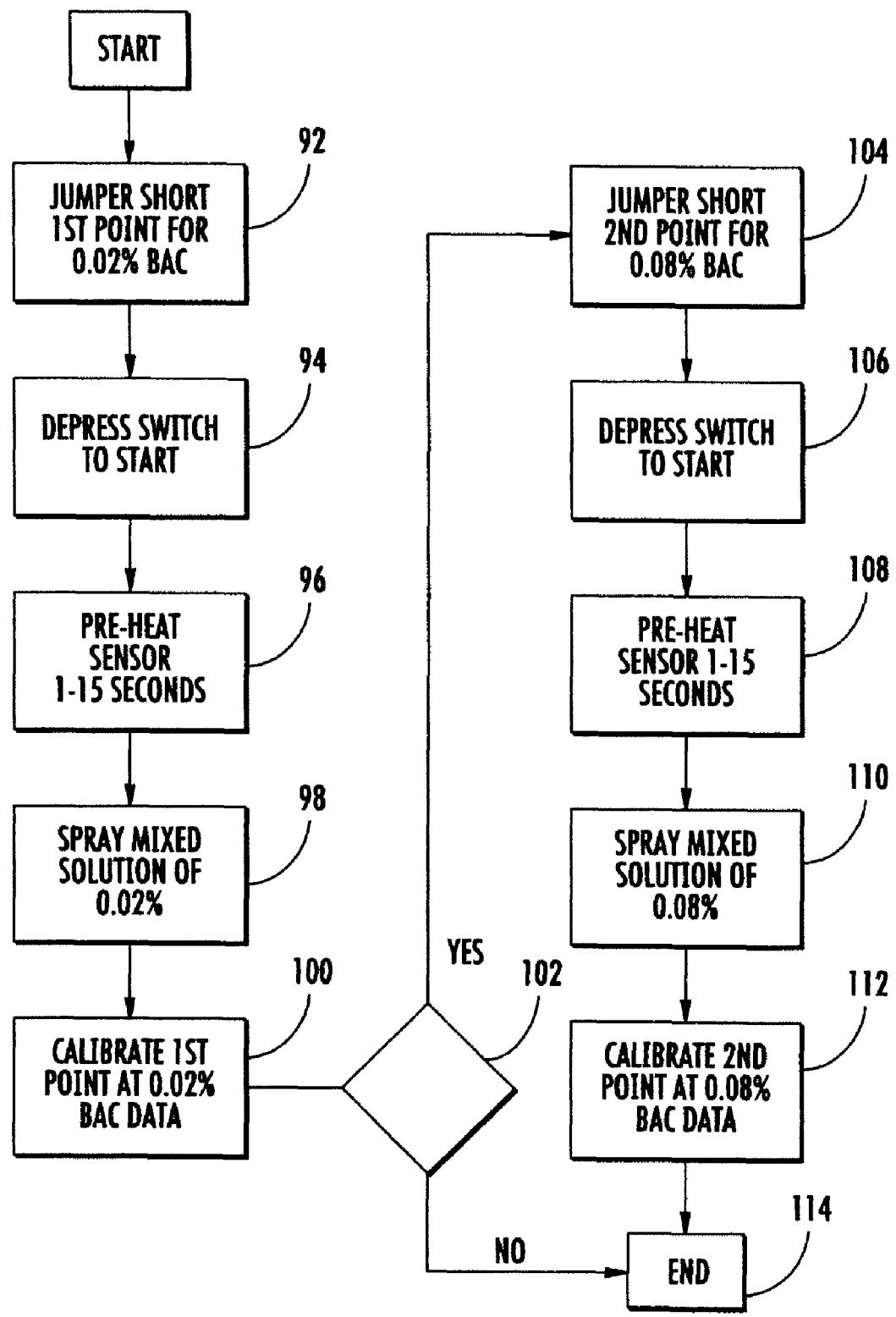
FIG. 7 shows a flow diagram of the steps of calibrating the breath tester of the present invention.

FIG. 7 shows a flow diagram of the calibration process of the present invention. Referring to FIGS. 2 and 7, calibration begins by jumper shorting 92 the input pin P71 (Port 28) of the microprocessor 32 as a first point of calibration for 0.02% blood alcohol content. Next 94, the switch 36 is depressed to provide power to the device 10. The Sensor Module 22 is preheated 96 for one to fifteen seconds, dependant on the last time the device 10 was used. Once the Sensor Module 22 is preheated, a mixing solution is prepared with distilled water and ethanol to a represent a known blood alcohol content. In the present example, the mixing solution is prepared to represent a 0.02% blood alcohol content and is sprayed 98 on the Sensor Module. The microprocessor 32 is then calibrated with the 0.02% blood alcohol content data 100. If the device is not to be calibrated for 0.08% blood alcohol content (decision 102), the calibration process is complete, and the process ends 114.

Otherwise, when the device 10 is to be calibrated for 0.08% blood alcohol content as well, input pin P72 (Port 27) of the microprocessor 32 is jumper shorted at a second point 104. Next 106, the switch 36 is depressed to provide power to the device 10. The Sensor Module 22 is again preheated 108 for one to fifteen seconds, dependant on the last time the device 10 was used. However the preheat period should be relatively short because the device 10 was recently preheated for calibration of 0.02% blood alcohol content. Once the Sensor Module 22 is preheated, a mixing solution is prepared with distilled water and ethanol to a represent a 0.08% blood alcohol content and is sprayed 110 on the Sensor Module. The microprocessor 32 is then calibrated with the 0.08% blood alcohol content data 112 and the calibration process is complete 114.

Figure 8A:
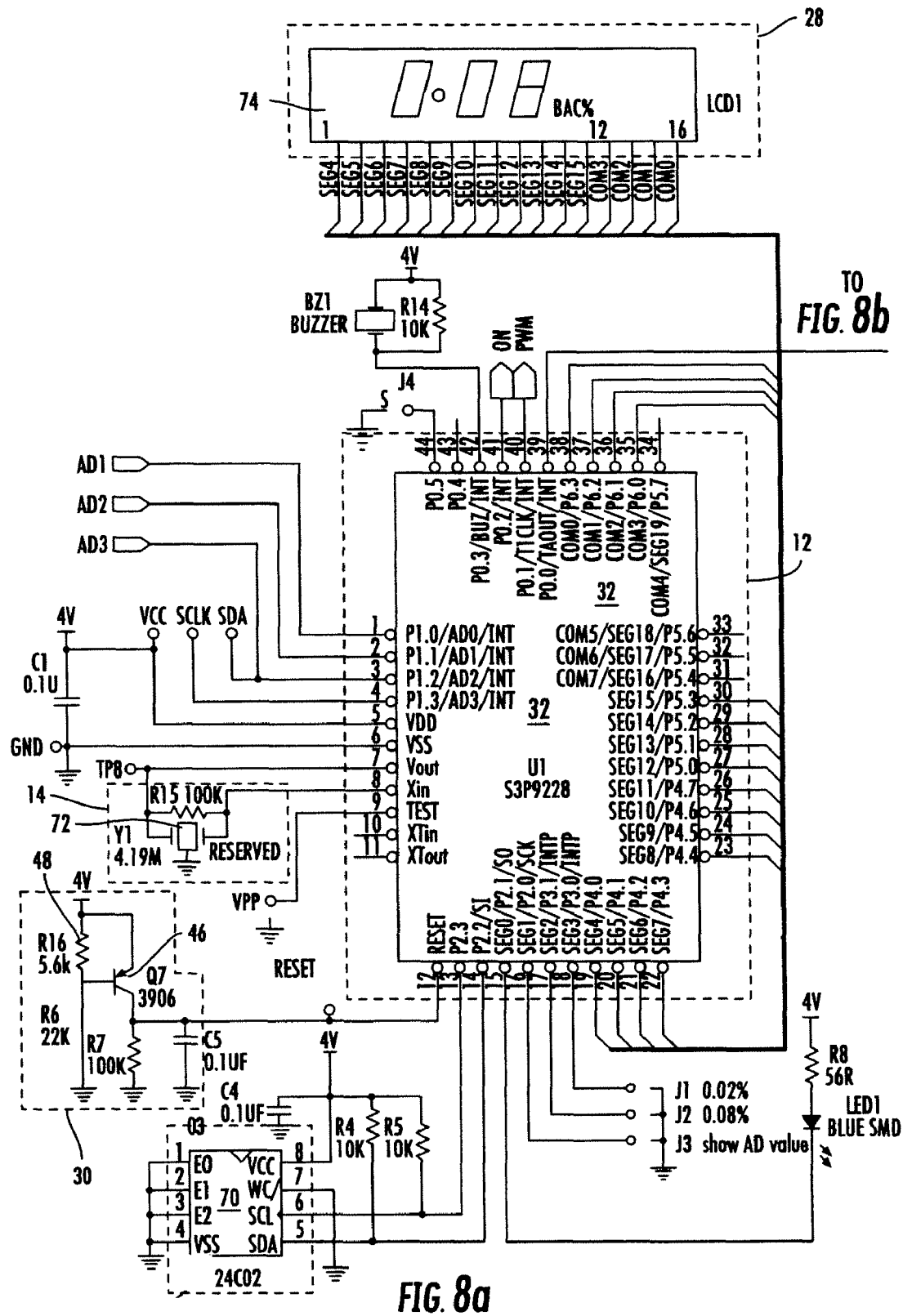
FIGS. 8a-b show a circuit schematic diagram of a breath tester system according to a second preferred embodiment of the present invention.
Figure 8B:
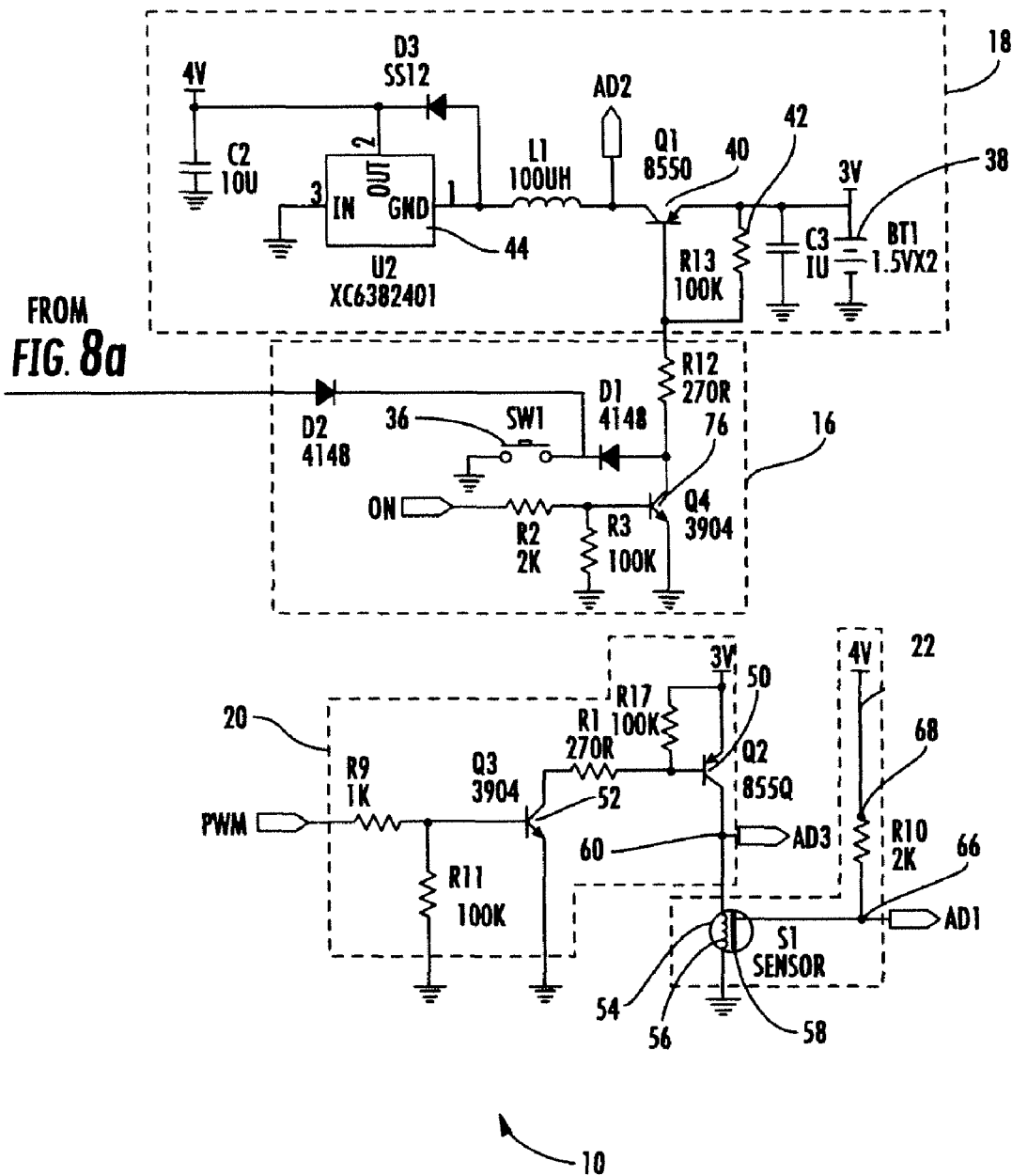

Referring to FIGS. 8a-b, a second preferred embodiment of the present invention is shown. The same reference numbers corresponding to similar circuit modules and circuit elements present in all preferred embodiments of the invention described herein will be utilized to describe the present preferred embodiment. As is seen in the circuit schematic of FIGS. 8a-b, the breath tester 10 comprises the following modules: Processor Module 12; Crystal Module 14; Switch Module 16; Power Module 18; Sensor Preheat Module 20; Sensor Module 22; Look-Up Reference Module 26; Display Module 28; and Reset Module 30. The individual modules have been organized and named for purposes of convenience in describing the structure and arrangement of components in a preferred embodiment and should not be considered as limiting in any manner.

Figure 9:
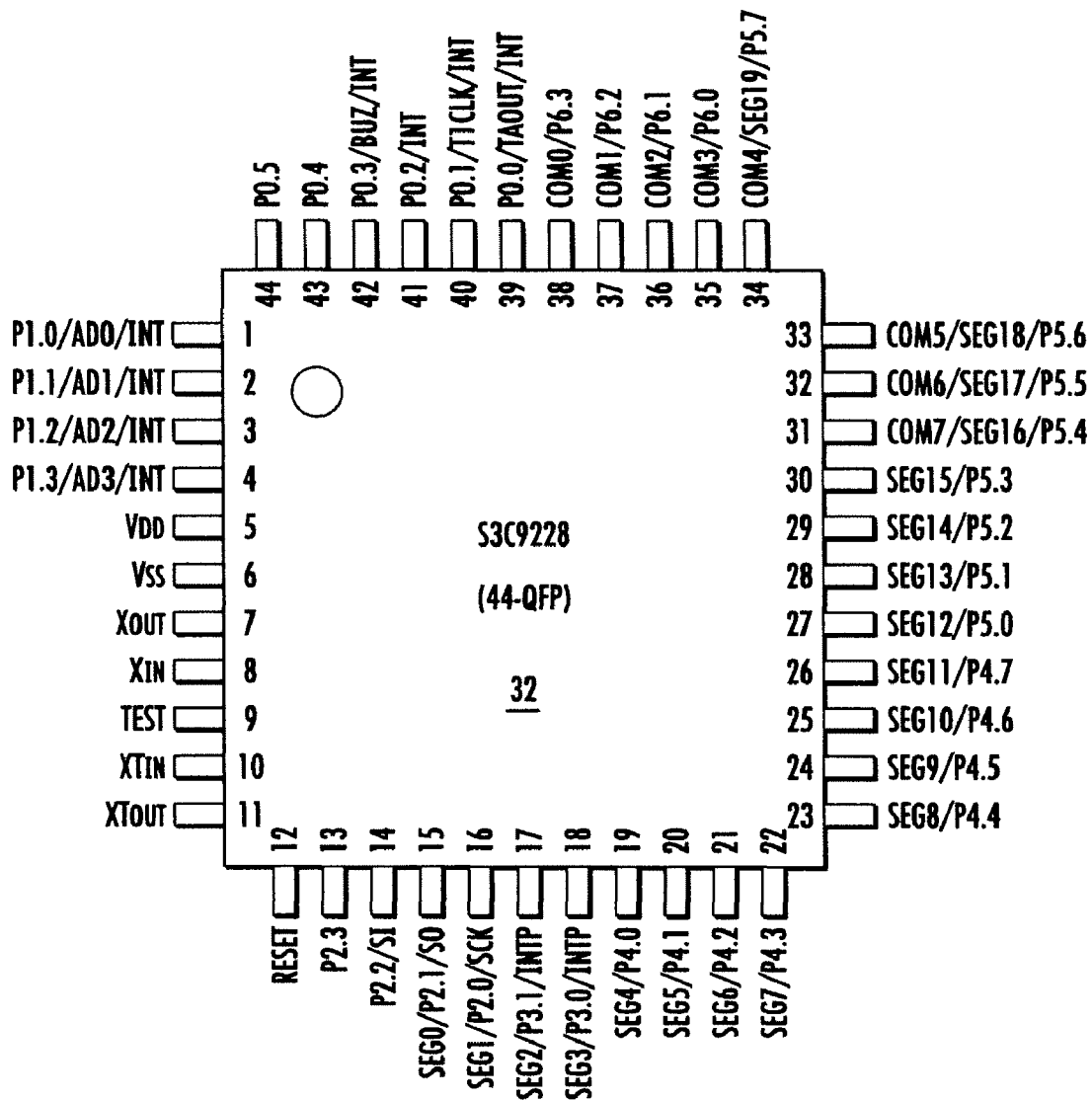
FIG. 9 shows a detailed schematic of the pin configuration of the microprocessor of a preferred embodiment of the present invention.
Figure 11:
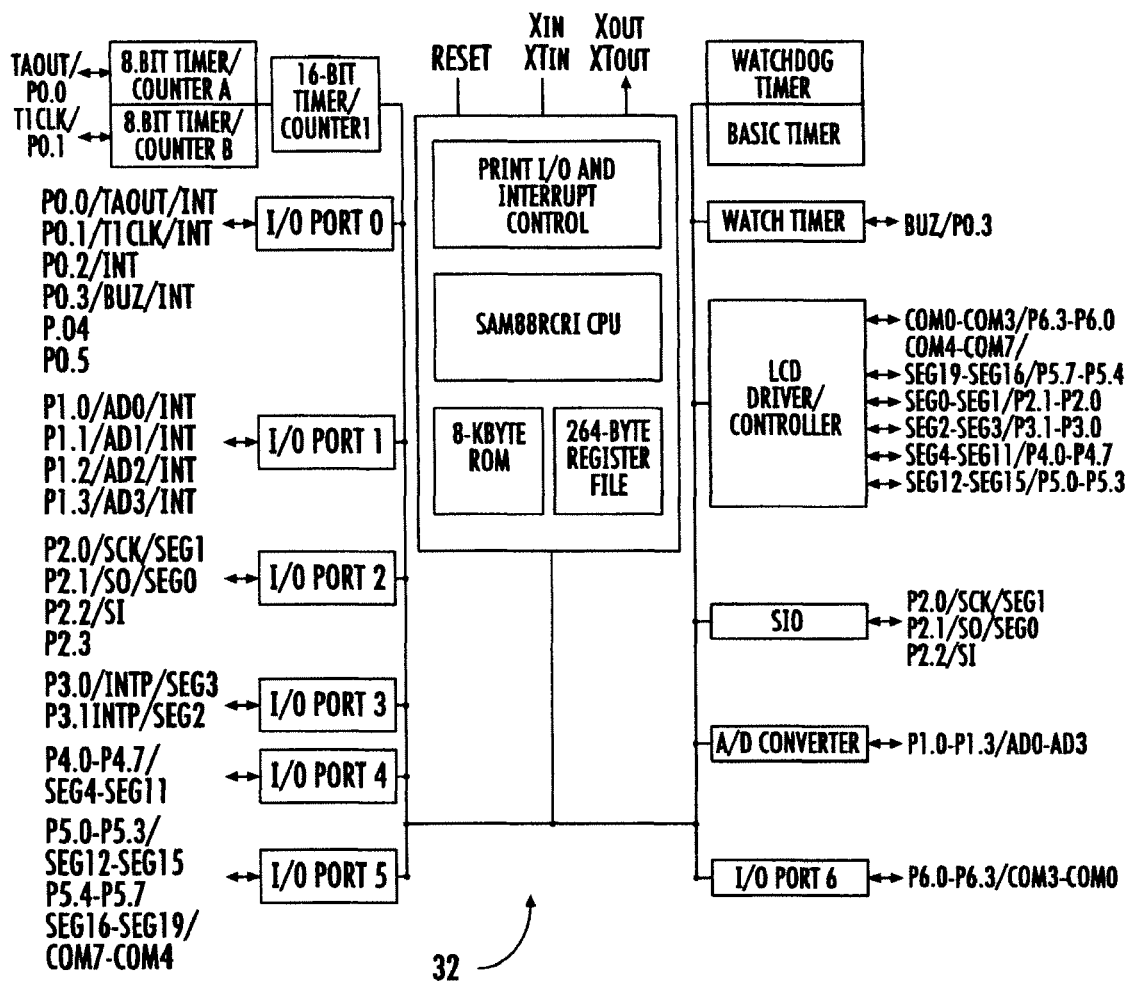
FIG. 11 is a block diagram of the microprocessor of a preferred embodiment of the present invention.

The Processor Module 12 is composed of a microprocessor chip 32. In a preferred embodiment of the present invention, the microprocessor 32 comprises an 8-bit chip with low power, high speed CMOS technology and having LCD controller/driver and pulse width modulation features. FIG. 9 shows the pin configuration of microprocessor 32 in detail and FIGS. 10a-10b show tables providing additional description of each pin on the microprocessor 32. FIG. 11 provides additional details of the microprocessor 32. The microprocessor 32 used in this preferred embodiment of the present invention is manufactured by Samsung Electronics Co., Ltd. and is sold as Product No. S3P9228. However, any suitable microprocessor can be utilized for purposes of the present invention.

Referring to the operation of the Switch Module 16 and Power Module 18 (shown in FIG. 8b), depressing the switch 36 will ground the positive terminal of the power source 38 causing a voltage to flow along the established pathway. The emitter end of the transistor 40 is coupled directly to the positive terminal of power source 38 and therefore receives voltage Vb from the power source 38. The base of the transistor 40 is coupled to the positive terminal of power source 38 across resistor 42. Accordingly the base end of transistor 40 receives a voltage of Vb minus the voltage drop across resistor 42. Because transistor 40 is in a P-N-P configuration and the voltage at the base is less than the voltage at the emitter, the transistor is biased closed, coupling the emitter and collector of transistor 40 and enabling Vb minus the voltage drop across transistor 40 to flow towards the step-up converter 44.

The step-up converter 44, steps up the input voltage signal to a voltage of +4V. The +4V voltage signal generated by the Power Module 18 is coupled to the components of the Processor Module 12 via the VDD power pin (Port 5), the Look-Up Reference Module 26, and the Reset Module 30. Voltage Vb from the power source 38 is coupled to the Sensor Preheat Module 20. In a preferred embodiment of the present invention the step-up converter 44 is a PFM controlled, step-up DCIDC converter manufactured by Torex Semiconductor and is sold under product number XC6382. The power source 3 is in this embodiment of the present invention two 1.5V DC batteries.

The Switch Module 16 also comprises an "electronic" switch that, when triggered, will enable the power source 38 to provide voltage to the device 10 if the user of the device releases the switch 36. The base of transistor 76 is coupled to the PO.2 input/output pin (Port 41) of microprocessor 32. Once powered up, the microprocessor 32 generates and sends an output voltage signal to the base of the transistor 76. Because transistor 76 is configured in the N-P-N configuration and the emitter is coupled to ground, the output voltage signal causes the transistor 76 to be biased closed, coupling the emitter and collector. Because the collector of transistor 76 is coupled to the base of the transistor 40, transistor 76 serves as an electronic switch, keeping transistor 40 biased closed to enable Vb from the positive terminal of power source 38 to supply a voltage to the Sensor Preheat Module 20 and the step-up converter 44. When the switch 36 is released and the microprocessor 32 terminates the power signal sent to the base of the base of transistor 76, then the power source 38 will not provide voltage to the components of the breath test device 10. The microprocessor 32 includes an automatic shut-off routine that terminates the power signal sent to the base of the transistor 76 after a preset period of inactivity.

Turning to the Reset Module 30 (shown in FIG. 8a), the emitter of transistor 46 is coupled directly to the +4V voltage signal from the step-up converter 44 of the Power Module 18. The voltage at the base of the transistor 46 comprises the +4V voltage signal from the step-up converter 44 minus the voltage drop across resistor 48. Because transistor 46 is in a P-N-P configuration, the transistor 46 is biased closed, coupling the emitter and collector and sending an input signal to the RESET pin (Port 12) of microprocessor 32 causing the breath tester circuit to reset itself and prepare to take a new reading. Turning to the Sensor Preheat Module 20 (shown in FIG. 8b), at one end of the module 20, the emitter of transistor 50 is coupled directly to the positive terminal of power source 38 and, therefore, has a voltage of Vb. The second end of the Sensor Preheat Module 20 is coupled to the PO.1 input/output pin (Port 1) of the microprocessor 32 and receives a pulsed power signal from the microprocessor 32. The breath tester circuit utilizes the pulse width modulation capability of the microprocessor 32 to control transistors 50 and 52 of the Sensor Preheat Module 20 and provide to the Sensor Module 22 constant voltage with a high current. The transistor 52 is configured in the N-P-N configuration with the emitter coupled to ground. Accordingly, providing a positive voltage signal to the base of transistor 52 will bias the transistor 52 closed, coupling the base of transistor 52 to ground.

The base of transistor 50 is also coupled to the collector of transistor 52 and is therefore responsive to the voltage signal at the collector of transistor 52. As is seen in the waveform diagrams of FIGS. 5a-5c, when the microprocessor 32 provides a pulse voltage signal to the Sensor Preheat Module 20 through the P0.1 pin, the transistor 52 is biased closed and the voltage at the collector is coupled to ground. Because the transistor 50 is in a P-N-P configuration, when the voltage at the base of transistor 50 is coupled to ground via transistor 52, the transistor 50 is biased closed, coupling the emitter and collector and providing a steady voltage to the Sensor Module 22. The pulsed output signal sent by the microprocessor 32 controls the operation of transistors 50 and 52 to provide a 0.9V equivalent DC voltage to the Sensor Module 22.

In a preferred embodiment of the present invention, the Sensor Module 22 comprises a tin dioxide semiconductor gas sensor 54. Tin dioxide sensors have high sensitivity to the presence of alcohol, however, it is contemplated that other suitable gas sensors are available and can be utilized in the present invention. The sensor 54 comprises a heating element 56 and a sensor element 58. The heating element 56 comprises a resistor having a first end coupled to the voltage output of the Sensor Preheat Module 20 and a second end coupled to ground. The sensing element 58 comprises a variable resistor having a conductivity that varies depending on the temperature of the sensor and the concentration of alcohol vapors present. A tin dioxide gas sensor manufactured by FiS, Inc. of Japan and sold as Product No. SB-30 is utilized in a preferred embodiment of the present invention.

In order to obtain optimum performance from the sensor 54 the voltage applied across the heating element 56 must be held steady. The sensor 54 of the present invention exhibits optimum performance when a voltage of 0.9V is applied to the heating element 56. As previously described, the components of the Sensor Preheat Module 20 are selected to provide a constant 0.9V to the heating element during operation of the breath test device 10 of the present invention. Reference point 60 is coupled to microprocessor 32 at P1.2/AD2/INT input/output pin (Port 3) to enable the microprocessor 32 to monitor the voltage at reference point 60. The output signal representing the voltage at the sensing element 58 is measured at reference point 66 adjacent to load resistor 68 and is coupled to the microprocessor 32 at the P1.0AD0/INT input/output pin (Port 1) for monitoring by the microprocessor 32.

In a preferred embodiment, the memory 70 of the Look-Up Reference Module 26 comprises an electrically erasable and programmable read-only memory (EEPROM) unit having at least 2048 bits of serial memory. An EEPROM suitable for use in the present invention is manufactured by Atmel Corp. and sold under Product No. AT2402C. The EEPROM 70 is used to store calibration data and look-up tables utilized by the microprocessor 32 during operation of the breath test device 10. The EEPROM is coupled to +4V output of the step up voltage converter 44.

The EEPROM 70 is used to store calibration and look-up table information used by the microprocessor 32 to calculate the blood alcohol content from the output voltage signal of the 20 sensing element 58. The breath tester device 10 is calibrated prior to use and may be recalibrated with new calibration and look-up table information being entered at the programming unit 34 and stored on the EEPROM 70. EEPROM 70 comprises a plurality of memory locations which serve as individually addressable reference registers containing values for the microprocessor to compare against the output of the sensing element during calibration and operation of the electronic breath analyzer. Data stored on the EEPROM 70 is clocked out to the microprocessor 32 at Serial Data (SDA) pin in response to receiving clocking input signals from the microprocessor 32 at the Serial Clock (SCL) pin. The SDA pin of the EEPROM 70 is coupled to the P2.2/S1 pin (Port 14) of the microprocessor 32. The SCL pin of the EEPROM 70 is coupled to the P2.3 pin (Port 13) of the microprocessor 32. The speed of the microprocessor 32, and in turn the clocking signal generated by the microprocessor 32 and received by the EEPROM 70, is determined by the oscillation of the crystal 72 of the Crystal Module 14. It is contemplated that any suitable crystal can be used in the present invention. While in this embodiment of the present invention, the memory 70 is a separate component than the microprocessor 32, it is contemplated that a microprocessor with sufficient internal memory can be utilized to perform the same functions as the separate memory and microprocessor configuration described herein.

The microprocessor 32 is also coupled to a Display Module 28. In a preferred embodiment of the present invention, the Display Module 28 comprises a liquid crystal display (LCD) 74. After performing the comparison of the data collected at reference point 60 against the date stored in EEPROM 70, the microprocessor 32 will cause the appropriate output to be displayed on the LCD 74. In the present embodiment, the LCD 74 displays the numeric value of the blood alcohol content of the user of the device 10. The LCD 74 is also used to display messages to the user of the device 10.

The circuit elements and arrangement described herein enables the breath tester device 10 of the present invention to address the need for a small, simple to use and convenient breath tester device. The circuitry can be packaged in a small housing to enable the breath tester to be extremely portable, such as a small attachment to key chain. The incorporation of the LCD results in the device conveying simple and clear instructions to the user of the device and simple and clear display of blood alcohol content. In addition, the selection of the specific electrical components described herein results in a system that works with minimal power requirements, prolonging the life of the power source and adding further to convenience of operation of the present device.

The foregoing description of an exemplary embodiment has been presented for purposes of illustration and description. It is not limited to be exhaustive nor to limit the invention to the precise form disclosed. Obvious modifications or variations are possible in light of the above teachings. The embodiment described herein best illustrates the principles of the invention and its practical application to thereby enable one of ordinary skill in the art to best utilize the invention in various embodiments and with various modifications as are suited to the particular use contemplated. It is intended that the scope of the invention be defined by the claims appended hereto.

The invention claimed is:

1. An electronic breath analyzer comprising:
   a gas sensor for alcohol detection, the gas sensor having a heater and a gas sensing element;
   a micro controller including a general control output, a reference value input and a gas sensing element input, the gas sensing element input being coupled to the gas sensing element, the micro controller being adapted to provide an initiate reading and comprising signal at the general control output;
   a reference value register having a reference value pre-stored in the register, and having a read initiate input and reference value output;
   a general control module having a control input, a read register output, and an enable gas sensor output, the control input coupled to the general control output, the read register output coupled to the read initiate input and providing a read initiate signal upon receiving the initiate reading and comparison signal from the micro controller, the enable gas sensor output being coupled to the gas sensor and producing an enable signal upon receiving the initiate reading and comparison signal from the micro controller;
   wherein the gas sensor includes a resistor R5 coupled between the gas sensing element and the enable gas sensor output of the general control module, and the reference value register includes a memory device having the read initiate input and the reference value output, and the general control module includes a transistor having a base which provides the control input, and an emitter coupled to a VCC voltage and a collector coupled to a VCC power input of the register and to the enable gas sensor output.

2. The electronic breath analyzer Of claim 1, wherein the read initiate input of the general control module is a VCC pin of the memory device, the reference value register includes a plurality of address inputs hardwired to correspond to a specific address, the transistor is an NPN transistor and has a resistor R15 coupled between a base of the transistor and an emitter of the transistor, and a resistor R16 is coupled between the base of the transistor of the general control module and the general control output of the micro controller.

3. The electronic breath analyzer of claim 2, wherein resistor R15 is 100K ohms and resistor R16 is 4.7K ohms, and the reference value register includes a clock input, the micro controller includes a clock output coupled to the clock input, and the micro controller outputs a pulse clock signal at the clock output to shift the reference value serially from the reference value output.

4. The electronic breath analyzer of claim 3, further comprising a first and second stage transistor circuit coupled to the gas sensor heater, the transistor circuit when activated preheating the heater.

* * * * *